United States Patent
Watson

(10) Patent No.: US 12,324,561 B2
(45) Date of Patent: *Jun. 10, 2025

(54) DISTORTION CORRECTION OF ENDOSCOPIC IMAGES IN COMPUTER-ASSISTED TELE-OPERATED SURGERY

(71) Applicant: INTUITIVE SURGICAL OPERATIONS, INC., Sunnyvale, CA (US)

(72) Inventor: Jason Paul Watson, San Jose, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/600,331

(22) Filed: Mar. 8, 2024

(65) Prior Publication Data

US 2024/0298872 A1  Sep. 12, 2024

Related U.S. Application Data

(63) Continuation of application No. 17/270,316, filed as application No. PCT/US2019/046614 on Aug. 15, 2019, now Pat. No. 11,963,658.
(Continued)

(51) Int. Cl.
*G06T 5/00* (2024.01)
*A61B 1/00* (2006.01)
(Continued)

(52) U.S. Cl.
CPC .... *A61B 1/000094* (2022.02); *A61B 1/00045* (2013.01); *G06T 5/70* (2024.01);
(Continued)

(58) Field of Classification Search
CPC ............. G06T 5/80; G06T 2207/10068; G06T 7/0012; G06T 1/00; G06T 5/70;
(Continued)

(56) References Cited

U.S. PATENT DOCUMENTS 5,704,897 A   1/1998  Truppe
6,720,988 B1  4/2004  Gere et al.
(Continued)

FOREIGN PATENT DOCUMENTS

EP       2186466 A1      5/2010
EP       2698983 A1      2/2014
WO     WO-2011077861 A1  6/2011

OTHER PUBLICATIONS

Lee, Tung-Ying, et al. "Automatic distortion correction of endoscopic images captured with wide-angle zoom lens." IEEE Transactions on Biomedical Engineering 60.9 (2013): 2603-2613.*
(Continued)

*Primary Examiner* — Li Liu
(74) *Attorney, Agent, or Firm* — Haynes & Boone, LLP.

(57) ABSTRACT

A surgical system may comprise a display device and an endoscope. The surgical system may also include a processing device configured to operate the surgical system to perform a process comprising receiving a source image and receiving a gaze location of a user of the surgical system. The process may also comprise determining a first region of the source image based on the gaze location. A second region of the source image partially surrounds the first region and includes a source distortion. The process may also comprise applying a distortion correction to the source image to generate a modified image by applying a first degree of distortion correction in the first region and a second degree of distortion correction in the second region. The second degree of distortion correction preserves the
(Continued)

source distortion in a portion of the second region. The process may also comprise displaying the modified image.

20 Claims, 7 Drawing Sheets

Related U.S. Application Data

(60) Provisional application No. 62/720,987, filed on Aug. 22, 2018.

(51) Int. Cl.
    *G06T 5/70*     (2024.01)
    *G06T 5/80*     (2024.01)
    *G06T 7/00*     (2017.01)

(52) U.S. Cl.
    CPC .............. *G06T 5/80* (2024.01); *G06T 7/0012* (2013.01); *G06T 2207/10068* (2013.01)

(58) Field of Classification Search
    CPC . G06T 3/047; A61B 1/00045; A61B 1/00009; A61B 1/00188; H04N 23/69
    See application file for complete search history.

(56) References Cited

U.S. PATENT DOCUMENTS

| | | |
|---|---|---|
| 11,963,658 B2 | 4/2024 | Watson |
| 2011/0069160 A1 | 3/2011 | Ning |
| 2011/0144482 A1* | 6/2011 | Sendai ................. G06T 7/0012 600/425 |
| 2014/0036050 A1 | 2/2014 | Yoshino |
| 2016/0105606 A1 | 4/2016 | Hikita et al. |
| 2018/0213153 A1 | 7/2018 | Iso et al. |
| 2018/0368656 A1 | 12/2018 | Austin et al. |
| 2021/0183025 A1 | 6/2021 | Watson |

OTHER PUBLICATIONS

Melo, Rui, Joao P. Barreto, and Gabriel Falcao. "A new solution for camera calibration and real-time image distortion correction in medical endoscopy-initial technical evaluation." IEEE Transactions on Biomedical Engineering 59.3 (2011): 634-644.*
International Preliminary Report on Patentability for Application No. PCT/2019/046614, mailed on Mar. 4, 2021, 09 pages.
International Search Report and Written Opinion for Application No. PCT/US2019/046614, mailed Feb. 4, 2020, 17 pages.
Smith, Warren E et al., "Correction of Distortion in Endoscope Images," IEEE Transactions on Medical Imaging, Mar. 1992, pp. 117-122, vol. 11—Issue 1, IEEE.
Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.
Zhang C., et al., "Nonlinear Distortion Correction in Endoscopic Video Images," Proceedings 2000 International Conference on Image Processing (Cat. No. 00CH37101), 2000, pp. 439-442.

* cited by examiner

DISTORTION CORRECTION OF ENDOSCOPIC IMAGES IN COMPUTER-ASSISTED TELE-OPERATED SURGERY

CROSS-REFERENCE TO RELATED APPLICATIONS

This application is a continuation of U.S. application Ser. No. 17/270,315, filed Feb. 22, 2021, which is a U.S. National Stage Application under 35 U.S.C. § 371 and claims the benefit of International Patent Application No. PCT/US2019/046614, filed on Aug. 15, 2019, which claims the benefit of priority to U.S. Provisional Application 62/720,987, filed on Aug. 22, 2018, the contents of which are incorporated herein by reference in their entirety.

TECHNICAL FIELD

This disclosure relates to devices and methods for minimally invasive computer-assisted tele-operated surgery.

BACKGROUND

Minimally invasive telesurgical systems for use in surgery are being developed to increase a surgeon's dexterity as well as to allow a surgeon to operate on a patient from a remote location. Telesurgery is a general term for surgical systems where the surgeon uses some form of remote control, e.g., a servomechanism, or the like, to manipulate surgical instrument movements rather than directly holding and moving the instruments by hand. In such a telesurgery system, the surgeon is provided with an image of the surgical site at the remote location. The surgeon performs the surgical procedures on the patient by manipulating master control input devices, which in turn control the motion of robotic instruments.

SUMMARY

This document describes a method of presenting an image of a portion of a surgical scene on a display device associated with an endoscope. The method includes receiving, from the endoscope, a source image representing a view of the surgical scene as captured using the endoscope. The method includes applying, by one or more processing devices, a distortion correction to at least a portion of the source image to generate a modified image, where the modified image includes a central region and a peripheral region surrounding the central region, and where a first degree of distortion correction in the central region is higher than a second degree of distortion correction in the peripheral region. The method includes presenting the modified image on the display device associated with the endoscope.

In some implementations, the distortion correction includes a correction function in which a degree of correction is a function of location with respect to a reference point in the image. In some implementations, the degree of correction varies non-linearly in the central region, and linearly in the peripheral region.

In some implementations, the method includes applying a smoothing correction to the modified image near a border of the central region, the smoothing correction resolving a discontinuity between the first degree of distortion correction in the central region and the second degree of distortion correction in the peripheral region.

In some implementations, the degree of correction in the peripheral region decreases from a boundary of the central region toward an outside edge of the peripheral region.

In some implementations, the method includes adjusting one or both of i) a size of the central region relative to a previous size of the central region and ii) a location of the central region relative to a center of the modified image. In some implementations, the method includes applying a zoom transform to the central region that magnifies a portion of the view of the surgical scene that is included in the central region of the modified image.

In some implementations, the central region overlaps a center of the modified image, and the peripheral region entirely surrounds the central region.

In some implementations, the method includes determining, based on signals received from one or more sensors, a particular region of the display device for positioning the central region. During application of the distortion correction to the source image, positioning the central region of the modified image to overlap the particular region.

In some implementations, the one or more sensors are configured to measure a gaze location of a user of the display device. The method further comprises determining the particular region of the display device based on the gaze location of the user. In some implementations, the one or more sensors are configured to detect a feature of the surgical scene of the source image, and the method further includes determining the particular region of the display device based on the detected feature. In some implementations, the one or more sensors are configured to determine a distance of a user from the display device, and the method includes determining the particular region of the display device based on the distance of the user from the display device.

In some implementations, the method includes processing the source image to identify an object represented in the source image, and during application of the distortion correction to the source image, positioning the central region of the modified image to overlap the object represented in the source image.

In some implementations, the source image represents a field of view extending laterally approximately 140 degrees. In some implementations, the central region represents a field of view extending laterally approximately 20-30 degrees. In some implementations, the central region is approximately elliptical.

In some implementations, the method includes receiving, from the endoscope, a digital image representing a distorted view of the surgical scene as captured using the endoscope. In some implementations, the method includes presenting a modified digital image on the display device associated with the endoscope. The modified digital image includes a central region that is substantially distortion-free and a peripheral region surrounding the central region. In some implementations, the peripheral region is distorted. In some implementations, a field of view of the digital image is substantially the same as a field of view of the modified digital image.

In some implementations, the source image is a digital image. In some implementations, applying, by the one or more processing devices, the distortion correction to at least the portion of the source image includes applying a transform to digital data of the portion of the source image.

This document describes a system including a display device, an endoscope, and one or more processing devices configured to operate the surgical system to perform a process (e.g., a surgical process). The process includes receiving, from the endoscope, a source image representing a view of a surgical scene as captured using the endoscope. The process includes applying a distortion correction to at least a portion of the source image to generate a modified image. The modified image includes a central region and a peripheral region surrounding the central region. A first degree of distortion correction in the central region is higher than a second degree of distortion correction in the peripheral region. The process includes presenting the modified image on the display device associated with the endoscope.

This document describes one or more machine-readable non-transitory storage devices encoded with machine-readable instructions configured to cause one or more processing devices to perform operations. The operations include receiving, from an endoscope, a source image representing a view of a surgical scene as captured using the endoscope. The operations include applying a distortion correction to the source image to generate a modified image. The modified image includes a central region and a peripheral region surrounding the central region and a first degree of distortion correction in the central region is higher than a second degree of distortion correction in the peripheral region. The operations include presenting the modified image on a display device.

Some or all of the embodiments described herein may provide one or more of the following advantages. A portion of the image provided during telesurgery operations can be corrected without discarding information at or near a periphery of the image. The information near the periphery of the image can be retained to enable the user to have a situational awareness of what is included in a surgical scene represented in the periphery of the image. The advantage of using a high field of view image is retained because the field of view is maintained. Distortions introduced to enable the high field of view are removed in portions of the image where detailed surgical work is to be performed. The distortions are corrected so that a portion of the high field of view image represents the surgical scene with spatial accuracy and is substantially distortion-free.

DETAILED DESCRIPTION

Figure 1:
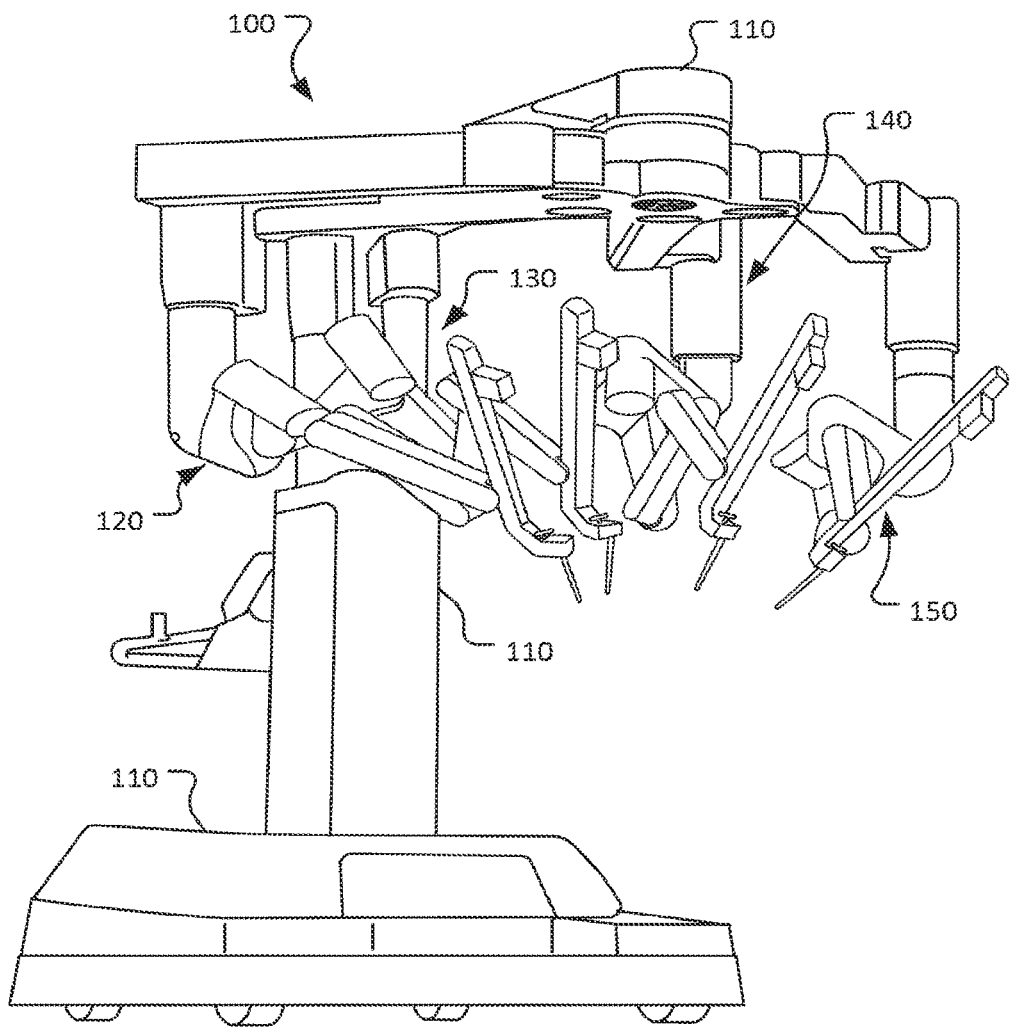
FIG. 1 is a perspective view of an example patient-side cart of a computer-assisted tele-operated surgery system.

This document describes technology that, in some cases, improves visualization of surgical sites and anatomical parts during image-guided surgical processes such as minimally invasive robot-assisted surgery (also referred to herein as minimally invasive surgery (MIS)). High field of view endoscope cameras can generate a distorted view of a surgical scene. The distorted view includes a greater field of view of the surgical scene than a corresponding image that is not distorted. For example, the distorted view can include a fish-eye lens effect (which gives the image a convex non-rectilinear appearance), caused by an ultra-wide-angle lens of the camera. While such images provide a wide field of view, the images are often not directly usable to provide visual feedback to surgeons during a live surgery. Rather, for such live use, the distortion is corrected (e.g., by image processing) so that a true (e.g., substantially distortion-free, high-fidelity, etc.) representation of at least a portion (e.g., region) of the surgical scene is presented on a display device associated with (e.g., in communication with) the endoscope. In some cases, the original image may be referred to as a source image, and the image including the undistorted portion can be referred to as a modified image. The correction of the distortion introduced by the camera lens can be referred to as a dewarping effect, image processing for dewarping, a distortion correction, and so forth. The magnitude of the distortion correction is referred to as the degree of correction and/or degree of distortion correction. For example, when a first magnitude of correction is applied to a first portion of the source image that is greater than a second magnitude of correction applied to a second portion for the source image, the first correction is referred to as a higher degree of correction, greater degree of correction, etc.

In some cases, dewarping of an entire image can have attendant negative consequences. For example, if the entire source image is corrected, information near the edges of the source image may be lost because the modified image cannot fit into the same size display as the distorted source image, unless some other alteration (shrinking, zooming out, reducing resolution, etc.) is also applied. To avoid losing information at the periphery of the source image due to the correction process, the technology described herein includes correcting only a portion of the source image (e.g., a 20°-30° central region in the field of vision), rather than the entire source image. In other words, a distortion correction is applied to a central region of the source image, while preserving (or in some cases, even increasing) at least some of the distortion in the periphery of the source image. This way, the central region of the image provides substantially distortion-free visual feedback to the surgeon, while preserving the information in the peripheral regions to provide situational awareness associated with the surgeon's peripheral vision.

In some implementations, the peripheral region of the image is further distorted to ensure that no portion of the source image is lost in the modified image and/or to ensure a smooth transition from the corrected central region and the distorted peripheral region. The modified image, including the central region and the peripheral region, is presented on a display device associated with the endoscope. In some implementations, the central region of the modified image is located in a portion of the surgical scene that is of particular interest (e.g., a region of the image where a surgical task is taking place). The location of the central region can be determined based on signals received from one or more sensors of the surgical device. For example, the location of the central region in the modified image can be moved (e.g., dynamically adjusted, updated, etc.) automatically based on feedback obtained from the one or more sensors and/or based on input from a user of the display device.

Aspects of the invention are described primarily in terms of an implementation using a da Vinci® Surgical System, commercialized by Intuitive Surgical, Inc. of Sunnyvale, California. Examples of such surgical systems are the da Vinci® Xi™ Surgical System (Model IS4000) and the da Vinci® Si™ HD™ Surgical System (Model IS3000). It should be understood that aspects disclosed herein may be embodied and implemented in various ways, including computer-assisted, non-computer-assisted, and hybrid combinations of manual and computer-assisted embodiments and implementations. Implementations on da Vinci® Surgical Systems (e.g., the Model IS4000, the Model IS3000, the Model IS2000, the Model IS1200) are described for illustrative purposes, and are not to be considered as limiting the scope of the inventive aspects disclosed herein. As applicable, inventive aspects may be embodied and implemented in both relatively smaller, hand-held, hand-operated devices and relatively larger systems that have additional mechanical support, as well as in other embodiments of computer-assisted tele-operated medical devices.

Figure 2A:
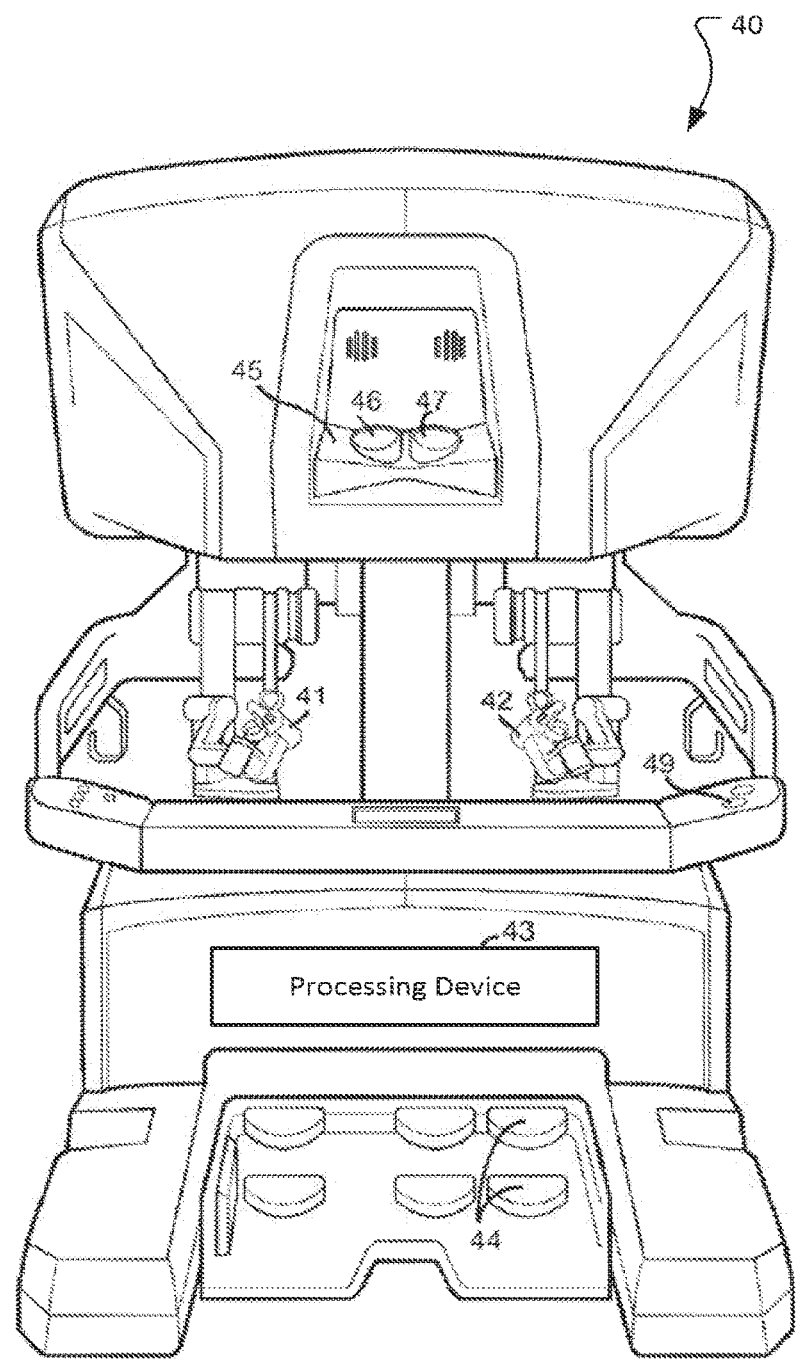
FIG. 2A is a front view of an example surgeon console of a computer-assisted tele-operated surgery system.

Referring to FIGS. 1 and 2A, systems for minimally invasive computer-assisted telesurgery (also referred to as MIS) can include a patient-side cart 100 and a surgeon console 40. Telesurgery is a general term for surgical systems where the surgeon uses some form of remote control, e.g., a servomechanism, or the like, to manipulate surgical instrument movements rather than directly holding and moving the instruments by hand. The robotically manipulatable surgical instruments can be inserted through small, minimally invasive surgical apertures to treat tissues at surgical sites within the patient body, avoiding the trauma associated with rather large incisions required for open surgery. These robotic systems can move the working ends of the surgical instruments with sufficient dexterity to perform quite intricate surgical tasks, often by pivoting shafts of the instruments at the minimally invasive aperture, sliding of the shaft axially through the aperture, rotating of the shaft within the aperture, and/or the like.

In the depicted embodiment, the patient-side cart 100 includes a base 110, a first robotic manipulator arm assembly 120, a second robotic manipulator arm assembly 130, a third robotic manipulator arm assembly 140, and a fourth robotic manipulator arm assembly 150. Each robotic manipulator arm assembly 120, 130, 140, and 150 is pivotably coupled to the base 110. In some embodiments, fewer than four or more than four robotic manipulator arm assemblies may be included as part of the patient-side cart 100. While in the depicted embodiment the base 110 includes casters to allow ease of mobility, in some embodiments the patient-side cart 100 is fixedly mounted to a floor, ceiling, operating table, structural framework, or the like.

In a typical application, two of the robotic manipulator arm assemblies 120, 130, 140, or 150 hold surgical instruments and a third holds a stereo endoscope. The remaining robotic manipulator arm assembly is available so that a third instrument may be introduced at the work site. Alternatively, the remaining robotic manipulator arm assembly may be used for introducing a second endoscope or another image-capturing device, such as an ultrasound transducer, to the work site.

Each of the robotic manipulator arm assemblies 120, 130, 140, and 150 is conventionally formed of links that are coupled together and manipulated through actuatable joints. Each of the robotic manipulator arm assemblies 120, 130, 140, and 150 includes a setup arm and a device manipulator. The setup arm positions its held device so that a pivot point occurs at its entry aperture into the patient. The device manipulator may then manipulate its held device so that it may be pivoted about the pivot point, inserted into and retracted out of the entry aperture, and rotated about its shaft axis.

In the depicted embodiment, the surgeon console 40 includes a stereo vision display 45 so that the user may view the surgical work site in stereo vision from images captured by the stereoscopic camera of the patient-side cart 100. Left and right eyepieces, 46 and 47, are provided in the stereo vision display 45 so that the user may view left and right display screens inside the display 45 respectively with the user's left and right eyes. While viewing typically an image of the surgical site on a suitable viewer or display, the surgeon performs the surgical procedures on the patient by manipulating master control input devices, which in turn control the motion of robotic instruments.

The surgeon console 40 also includes left and right input devices 41, 42 that the user may grasp respectively with his/her left and right hands to manipulate devices (e.g., surgical instruments) being held by the robotic manipulator arm assemblies 120, 130, 140, and 150 of the patient-side cart 100 in preferably six or more degrees-of-freedom ("DOF"). Foot pedals 44 are provided on the surgeon console 40 so the user may control movement and/or actuation of devices associated with the foot pedals.

A processing device 43 is provided in the surgeon console 40 for control and other purposes. The processing device 43 performs various functions in the medical robotic system. One function performed by processing device 43 is to translate and transfer the mechanical motion of input devices 41, 42 to actuate their corresponding joints in their associated robotic manipulator arm assemblies 120, 130, 140, and 150 so that the surgeon can effectively manipulate devices, such as the surgical instruments. Another function of the processing device 43 is to implement the methods, cross-coupling control logic, and controllers described herein. The processing device 43 can include one or more processors, digital signal processors (DSPs), field-programmable gate arrays (FPGAs), and/or microcontrollers, and may be implemented as a combination of hardware, software and/or firmware. In addition, its functions as described herein may be performed by one unit or divided up among a number of subunits, each of which may be implemented in turn by any combination of hardware, software and firmware. Further, although being shown as part of or being physically adjacent to the surgeon console 40, the processing device 43 may also be distributed as subunits throughout the telesurgery system. One or more of the subunits may be physically remote (e.g., located on a remote server) to the telesurgery system.

Figure 2B:
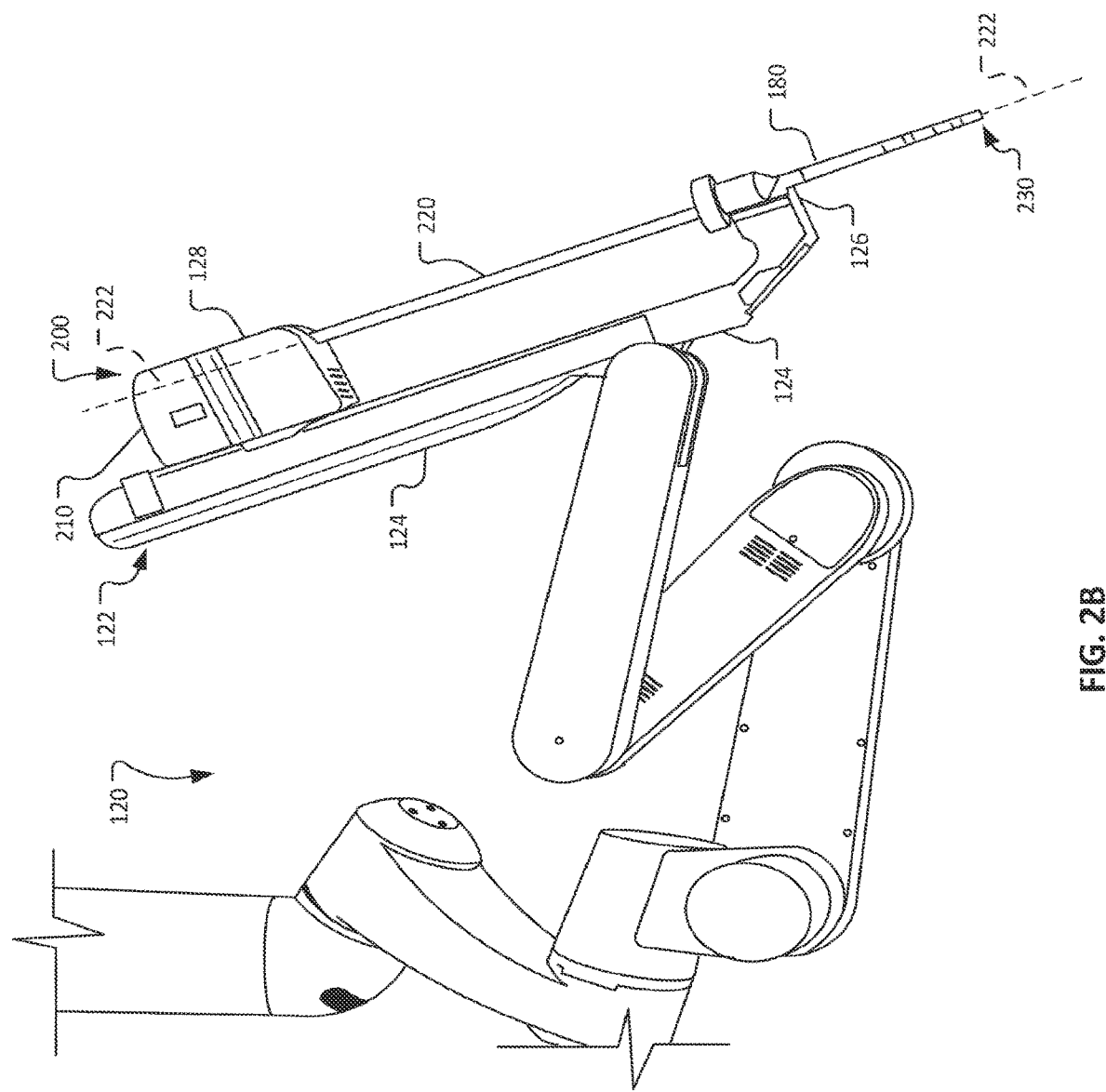
FIG. 2B is a side view of an example robotic manipulator arm assembly of a computer-assisted tele-operated surgery system.

Referring also to FIG. 2B, the robotic manipulator arm assemblies 120, 130, 140, and 150 can manipulate devices such as surgical instruments to perform MIS. For example, in the depicted arrangement the robotic manipulator arm assembly 120 is pivotably coupled to an instrument holder 122. A cannula 180 and a surgical instrument 200 are releasably coupled to the instrument holder 122. The cannula 180 is a hollow tubular member that is located at the patient interface site during a surgery. The cannula 180 defines a lumen in which an elongate shaft 220 of the surgical instrument 200 is slidably disposed. As described further below, in some embodiments the cannula 180 includes a distal end portion with a body wall retractor member. The instrument holder 122 is pivotably coupled to a distal end of the robotic manipulator arm assembly 120. In some embodiments, the pivotable coupling between the instrument holder 122 and the distal end of robotic manipulator arm assembly 120 is a motorized joint that is actuatable from the surgeon console 40 and processor 43.

The instrument holder 122 includes an instrument holder frame 124, a cannula clamp 126, and an instrument holder carriage 128. In the depicted embodiment, the cannula clamp 126 is fixed to a distal end of the instrument holder frame 124. The cannula clamp 126 can be actuated to couple with, or to uncouple from, the cannula 180. The instrument holder carriage 128 is movably coupled to the instrument holder frame 124. More particularly, the instrument holder carriage 128 is linearly translatable along the instrument holder frame 124. In some embodiments, the movement of the instrument holder carriage 128 along the instrument holder frame 124 is a motorized, translational movement that is actuatable/controllable by the processor 43. The surgical instrument 200 includes a transmission assembly 210, the elongate shaft 220, and an end effector 230. The transmission assembly 210 may be releasably coupled with the instrument holder carriage 128. The shaft 220 extends distally from the transmission assembly 210. The end effector 230 is disposed at a distal end of the shaft 220.

The shaft 220 defines a longitudinal axis 222 that is coincident with a longitudinal axis of the cannula 180. As the instrument holder carriage 128 translates along the instrument holder frame 124, the elongate shaft 220 of the surgical instrument 200 is moved along the longitudinal axis 222. In such a manner, the end effector 230 can be inserted and/or retracted from a surgical workspace within the body of a patient.

Figure 3:
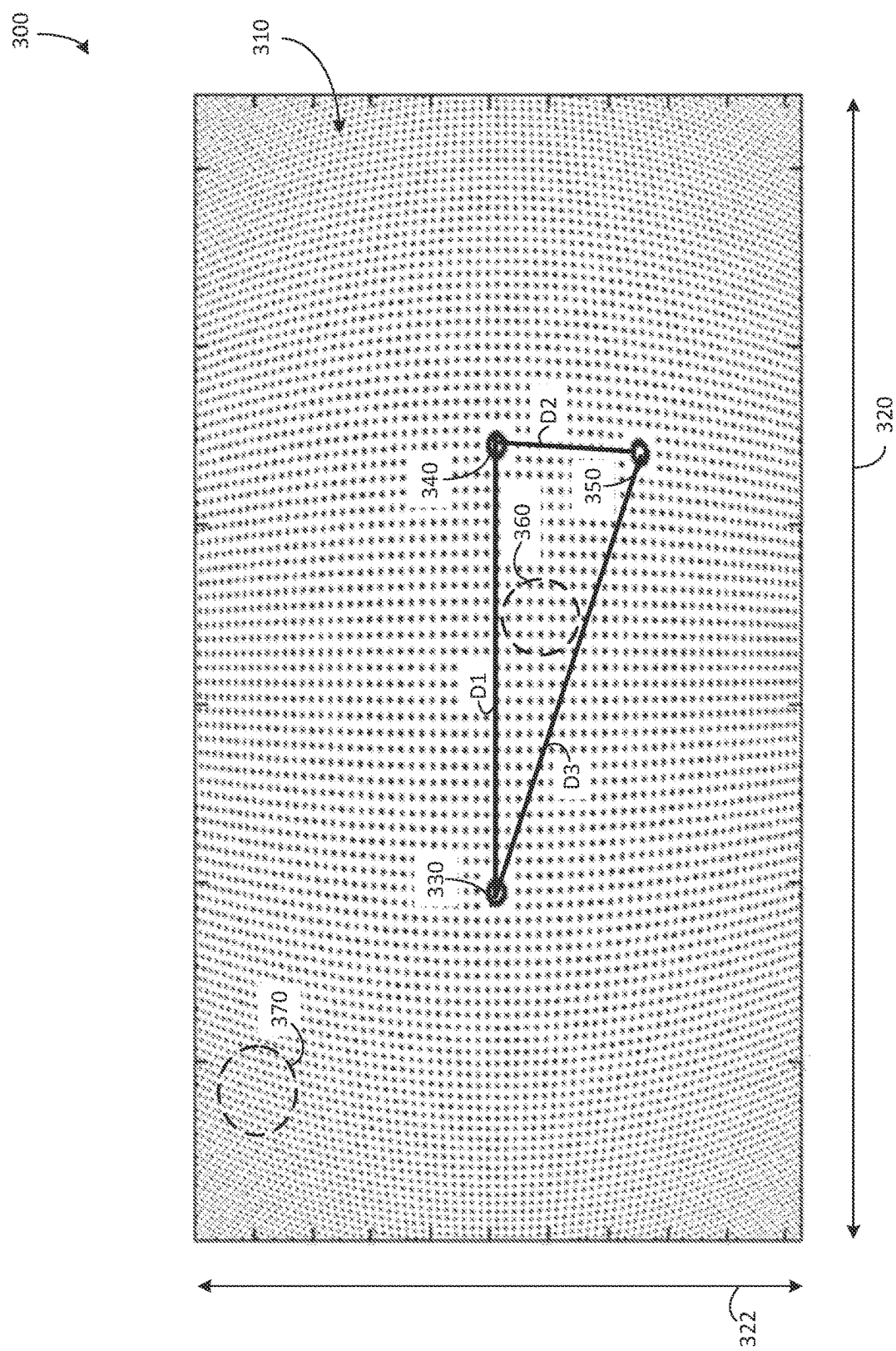
FIG. 3 shows a representation of a source image.

The display 45 of the surgeon console 40 is configured to present images of the surgical scene that are captured using the endoscope. The images captured by the endoscope (called source images) are displayed to enable the user to operate the instruments described above. Referring to FIG. 3, a representation 300 (e.g., a model) of a source image is shown. While an actual source image is not shown, a matrix-of-dots 310 (which may also be referred to as a matrix) is included to illustrate distortions of the surgical scene depicted in the source image. In some implementations, the source image is shown on the display 45 of the surgeon console 40. The source image is captured by an instrument of the telesurgery system. In some implementations, the instrument (not shown) includes a camera. In some implementations, the camera includes an endoscopic camera. In some implementations, the camera is attached to one of robotic manipulator arm assemblies 120, 130, 140, or 150 (e.g., described in relation to FIG. 2B).

The matrix 310 represents sample locations that are approximately equidistant from each other in a surgical scene represented in the source image. Dots of the matrix 310 do not correspond to pixels in the source image, but rather illustrate how the source image is distorted. For example, in a first region 360 near a center of the representation 300, consecutive dots of the matrix 310 are approximately equidistant. However, consecutive dots of the matrix 310 in a second region 370 are not equidistant. The changes in distances between the dots of the matrix 310 in region 370 (and throughout the dot matrix) represent varying amounts of distortion in the depiction of a surgical scene in the source image. For comparison, where there is no distortion in the source image, consecutive dots of a representative matrix would be equidistant (or approximately equidistant).

For the matrix 310, the representation 300 is for a high field of view source image. The representation of the surgical scene is optically distorted (e.g., by a lens) to increase the field of view for the endoscope and result in a high field of view source image. In some implementations, the field of view is approximately 140 degrees. The range of the field of view of the source image can vary. In some implementations, the field of view is up to 180 degrees. In some implementations, the field of view is adjustable, e.g., automatically, by one or more controls of the telesurgery system, and/or by some combination of manual and automatic adjustment. In some cases, as the field of view increases, the optical distortion in the source image increases. In some implementations, the distortion in the source image may be represented using a mathematical model. For example, the distortion represented by the matrix 310 is approximately quadratic from the center of the representation 300 to the edges of the representation. In some implementations, the distortion represented by the matrix 310 includes a "fish-eye lens" effect. The representation 300 of the source image shows less distortion near a center of the source image (e.g., at and near region 360) as compared to near the edges of the source image (e.g., at and near region 370 and other edges and/or corners of the source image). In the representation 300 shown in FIG. 3, three dots 330, 340, and 350 of the matrix 310 are highlighted to illustrate the distortion in the representation. The distances D1, D2, and D3 represent the separation between the dots 330 and 340, the dots 340 and 350, and the dots 350 and 330, respectively, in a distorted source image. When the distortion in the source image is corrected (e.g., using a dewarping process), the corresponding distances in the corrected image are changed, as described below with reference to FIG. 4.

The distortion correction process described herein removes the distortion in a particular portion (referred to as the central region) of the source image, while preserving at least some distortion in portions outside the central region. In some implementations, the central region (also called a corrected region) includes an area of the modified image that is substantially at the center of the field-of-vision of the surgeon, and thus has to be substantially-distortion-free to provide accurate visual feedback to the surgeon during a surgical process. The remaining portion of the modified image (e.g., portions outside of the central region) includes a peripheral region that may only be in the peripheral view of the surgeon during a surgical process. In some implementations, some distortion in the peripheral region may be tolerable because information included in that region may be useful only for an overall situational awareness of the surgeon with respect to the surgical scene. However, in some cases, it may be important to preserve the information in the peripheral region (even if the representation of the information in the image is distorted) such that the field-of-view of the surgeon is not compromised. Preserving the large field of view can be particularly advantageous in endoscopic surgical systems, for example, to provide visual feedback on any bleeding that may not be occurring from a portion of tissue at the center of the field-of-vision of the surgeon.

The technology described herein allows for preserving the field-of-vision of the source image while providing a substantially distortion-free region near the center of the field of vision of the surgeon. For example, the peripheral region of the modified image can be left substantially uncorrected. In some implementations, additional distortion can be introduced in at least a portion of the peripheral region of the modified image. In some implementations, the corrected region of the modified image is at or near a center of the modified image (e.g., in accordance with the center of a field of vision of the surgeon). However, a location of the corrected region can be anywhere in the modified image. In some implementations, a location of the central region or corrected region can be changed adaptively, for example, based on determining a location of the center of the surgeon's field of vision. For example, the direction of gaze of the surgeon can be tracked to adaptively change the location of the central region of the modified image. In some implementations, the central or corrected region can include an edge of the modified image, and may be only partially surrounded by the peripheral region. In some such cases, at least a portion of the corrected region (e.g., portions near the edge of the image) may be discarded to accommodate corrections near the edge.

In some implementations, the endoscope may be oriented so that a surgical site is near a center of the source image, requiring a substantially distortion-free representation of the surgical scene near the center of the source image. Areas near the periphery of the image are retained. Rather than completely discarding information in the source image near the periphery of the source image, a distorted representation of the surgical scene is presented in the peripheral region of the modified image, enabling a user to maintain a situational awareness of what is represented in the periphery of the subject matter of the operation. This provides an environmental context to the corrected portion of the source image.

Figure 4:
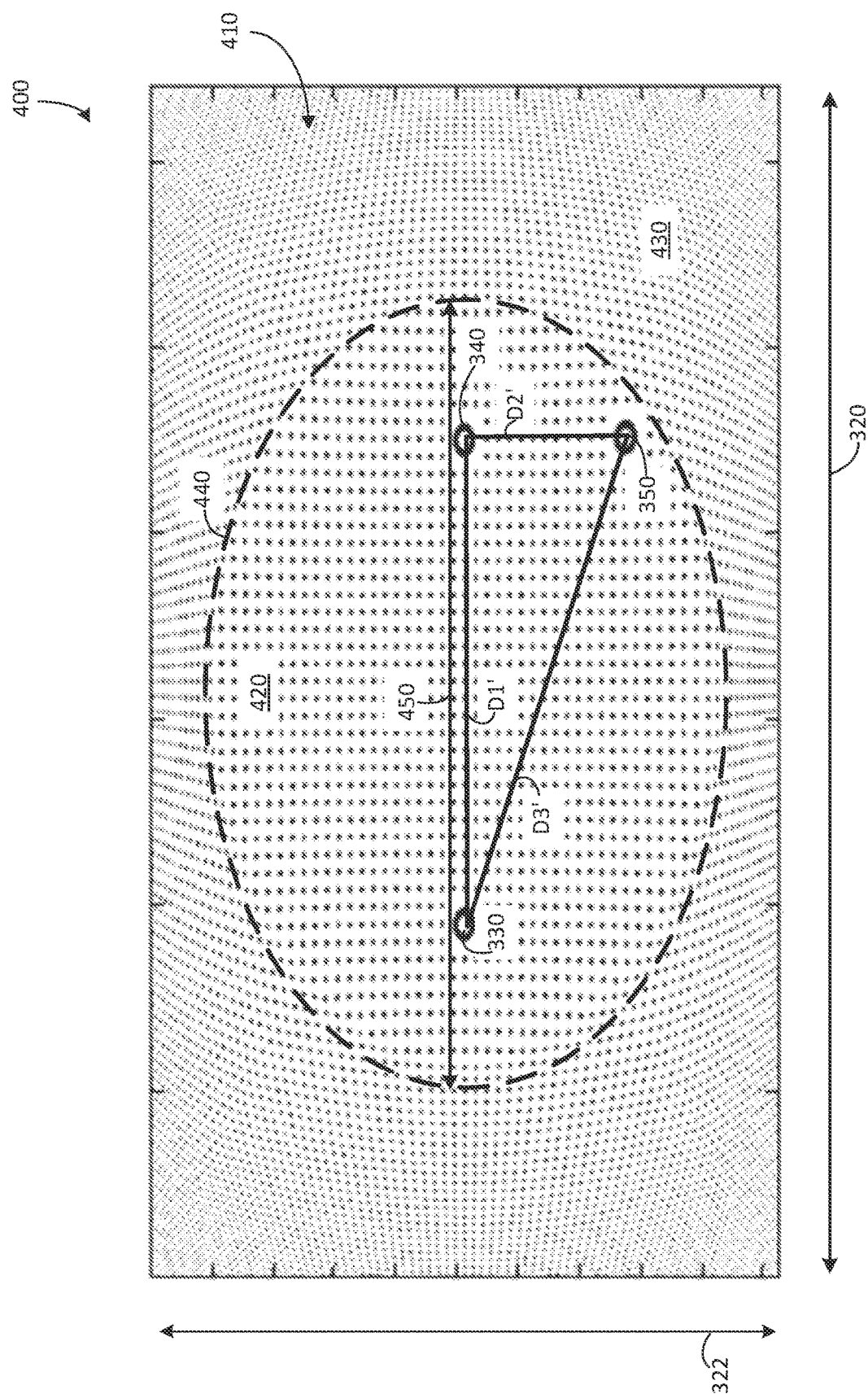
FIG. 4 shows a representation of a modified image.

Turning now to FIG. 4, a representation 400 of a modified image is shown after a distortion correction has been applied (e.g., by the processing device 43 of the telesurgery system or some other digital processing device associated with the telesurgery system). The representation 400 of the modified image includes a matrix-of-dots 410 (also referred to as a matrix), wherein consecutive dots represent approximately equidistant locations in the surgical scene.

The modified image can include two or more regions with different amount of distortion correction. In the example of FIG. 4, the modified image includes a central region 420 (e.g., the corrected region described above) and a peripheral region 430. The central region 420 and the peripheral region 430 are two regions of the modified image in which the levels of distortion correction are different. For example, in the central region 420 any distortion in the corresponding portions of the source image is substantially corrected. In the peripheral region 430, any distortion in the corresponding portions of the source image are preserved (or is further distorted) to preserve the high field of view information captured in the source image. The central region 420 can be distinguished from the peripheral region 430 using one or more techniques, described in further detail, below. The dashed line 440 of FIG. 4 represents a border between the central region 420 and the peripheral region 430. The dashed line 440 is shown in FIG. 4 for illustrative purposes only; such a line does not actually show up in an actual modified image.

Typically, distortion in the central region 420 of the modified image is corrected so that the central region 420 accurately represents the surgical scene (e.g., substantially without distortion, or with minimal distortion). Because the distortion of the source image is typically induced by optical elements (e.g., a lens assembly of a camera), the distortion is typically regular in nature, and may be removed substantially completely. In some implementations, at least a portion of the central region 420 is partially corrected, such that a distortion represented in the corresponding source image is not entirely removed. A partial correction of the central region 420 can be used, for example, when a complete correction is not required, to smooth the effects of correction over an extended portion of the source image including the periphery, and so forth. For example, if the distortion in the source image is not uniform (e.g., a distortion that cannot be represented using a computationally efficient model), complete correction of the distortions inside the central region 420 can be relatively computationally expensive when compared to correction of uniform distortions. In some implementations, implementing a partial correction to the central region 420 may reduce processing burden, e.g., by the use of a simple but approximate distortion correction. Such an approximate distortion correction process may be useful, for example, in cases where the fidelity of the representation of the surgical scene in the modified image is balanced against another performance criterion such as a frame rate of video (e.g., when the modified images are being transmitted to a remote display device) or computational latency associated with the distortion correction process.

The representation 400 of the modified image shows the central region 420, the peripheral region 430, and the updated positions of the dots 330, 340, 350 in the matrix 410. Consecutive dots of the matrix 410 are approximately equidistant in the central region 420, which represents the region of the modified image that is corrected (e.g., dewarped). The approximately equidistant consecutive dots inside the central region 420 indicate that the portion of the modified image inside the central region 420 is a true (e.g., substantially distortion-free) representation of the surgical scene. The distance between dot 330 and dot 340 is now D1' (rather than D1 as in FIG. 3). The distance between dot 340 and dot 350 is now D2' (rather than D2 as in FIG. 3). The distance between dot 330 and dot 350 is now D3' (rather than D3 as in FIG. 3). In this example, D1' is slightly longer than D1. However, in other cases (e.g., where the source image is distorted differently), D1' may be shorter than D1 or even substantially equal to D1. For example, if D1 is much longer or much shorter than D1', relatively greater degree of distortion correction is applied to the central region 420. Relatively, if D1 is slightly smaller or slightly longer than D1', a relatively lesser degree of distortion correction is applied to the central region 420. A similar comparison also applies between D2 and D2', and between D3 and D3'. In some implementations, dots in the peripheral region 430, which can be further distorted to enable retention of the entire extended field of view of the source image, may be closer together in the matrix 410 than in the matrix 310 of FIG. 3. Such a change represents further distortion of the source image in the peripheral region 430 in the generated modified image. In some implementations, the relative locations of the dots of matrix 410 in the peripheral region 430 are unchanged, indicating that no distortion correction is applied to the peripheral region 430. In some implementations, the peripheral region 430 can be left unmodified from the distorted source image in order to save processing resources while enabling situation awareness of what is in the surgical scene depicted in the peripheral region 430 of the modified image.

In short, distortions in the central region 420 of the modified image are corrected from the source image a first amount, and distortions in the peripheral region 430 of the modified image are corrected from the source image a second amount that is different from the first amount.

A geometry (e.g., size, shape, etc.) of the central region 420 is based on several different factors. As stated above, the field of view of a high field of view source image can be around 140 degrees, or up to 180 degrees. The field of view is represented by the lengths of the axes 320 and 322 in FIGS. 3 and 4. The field of view of the modified image is the same or approximately the same as the source image, preserving the peripheral representation of the surgical scene. The central region 420 region covers a percentage of the field of view of the source image, designated by width 450 in FIG. 4. In some implementations, the cross-section width 450 of the central region corresponds to about 10%-40% of the field of view of the modified image. In some implementations, the central region 420 corresponds to approximately 20-40 degrees in an overall field of view of 140-180 degrees. The relative field of view of the central region 420 to the peripheral region 430 can be increased or decreased depending on the field of view of the source image and the size of the display device 45 of FIG. 2A. For example, as the size of the central region 420 increases, the relative field of view of the central region 420 with respect to the entire field of view along axis 320 and axis 322 increases. The width 450 of the central region 420 may be constrained only by the size of the modified image. For example, because the entire source image cannot be corrected (e.g., dewarped) and displayed without some additional adjustment (e.g., zooming out, shrinking the size and/or reducing the resolution of the source image, etc.), the cross-section width 450 of the field of view of the central region may be constrained to a value less than that of the length of the corresponding axis 320.

While the central region 420 shown in the representation 400 of the modified image of FIG. 4 includes an ellipse, other shapes of the central region are possible. In some implementations, the shape of the central region 420 is based on the type of distortion and the shape of the source image. For example, the distortion shown in FIGS. 3-4 is radial-based, and thus an ellipse is symmetrical for correction of the distortion (e.g., at border 440 shown in FIG. 4). In other words, the distortion magnitude is symmetric in an elliptical pattern because the source image is rectangular and because the distortion is radial-based. However, if the source image is a different shape (e.g., square), the central region 420 may be circular. In some implementations, the central region 420 is another shape (square, rectangular, etc.).

The location of the central region 420 with respect to the center of the modified image is generally centered but may be adjusted to other positions in the modified image. In some implementations, the position of the central region 420 can be adjusted based on an input from a user of the telesurgery system. For example, one or more controls (not shown) can be used to indicate where the central region 420 should be located. In some implementations, the location of the central region 420 is preprogrammed. For example, the central region 420 can be fixed in the center of the modified image or at some other position in the modified image. In some implementations, the central region 420 is positioned at an edge of the modified image. In some implementations, the central region 420 is positioned at a corner of the modified image.

The position of the central region 420 can be adjusted in real-time. In some implementations, the position of the central region 420 is based on receiving one or more signals from a gaze-tracking interface (not shown) that is integrated into the left and right eyepieces, 46 and 47 of FIG. 2A. The gaze-tracking interface determines what part of the display device 45 is being viewed by a user of the telesurgery system, and dynamically moves the corrected central region 420 to be on the part of the display device at which the user is looking. For example, if the user is looking at a top-left part of the screen, the top-left portion of the modified image includes the central region 420. This can mean moving a central region 420 of a fixed size to the location being looked at, or it can mean expanding the central region 420 to cover the portion of the screen being looked at by the user. In some implementations, the position and/or size of the central region 420 can be adjusted based on a detected distance of a user from the display device 45. For example, if a user is far from the display device 45 (e.g., in cases where the display is a single screen), the central region 420 can be made larger.

In some implementations, the geometry of the central region 420 is adjusted automatically based on what is being displayed in the source image. For example, the telesurgery system processes the source image to determine that a feature is present in the image. The feature can include a surgical instrument, a biological feature, a subject of the surgery, or any such feature. For example, the feature can be selected by a user in advance of the telesurgery. The telesurgery system can be trained to recognize the feature, e.g. using a machine-learning technique. In some implementations, the feature can be recognized by other image processing techniques (e.g., pixel thresholding, line detection, etc.). Once the feature is recognized in the source image, the processing device 43 causes the central region 420 to include the feature. In some implementations, the feature is detected before distortion correction is applied to the source image.

In some implementations, the geometry of the central region 420 is adjusted automatically based on detecting a movement of a user and/or a feature of the surgical scene. For example, a surgical instrument shown in the source image can be tracked so that the central region 420 follows movement of the instrument around the surgical scene of the source image over several iterations of source images (e.g., when a video is taken). In another example, a motion sensor can track movement of a user of the telesurgery device and adjust the central region 420 based on the detected movement. When the user moves further from a display device (e.g., display device 45 of FIG. 2A), the central region can be enlarged on the display.

In some implementations, the surgical scene included in the central region 420 is further processed after being corrected. For example, the surgical scene included in the central region 420 can be magnified (e.g., by a zoom transform). To compensate for the magnified central region 420, the peripheral region 430 is further distorted and/or a resolution is reduced, preserving information for situational awareness with respect to the central region 420 without reducing the field of view along axis 320 and/or axis 322.

Figure 5:
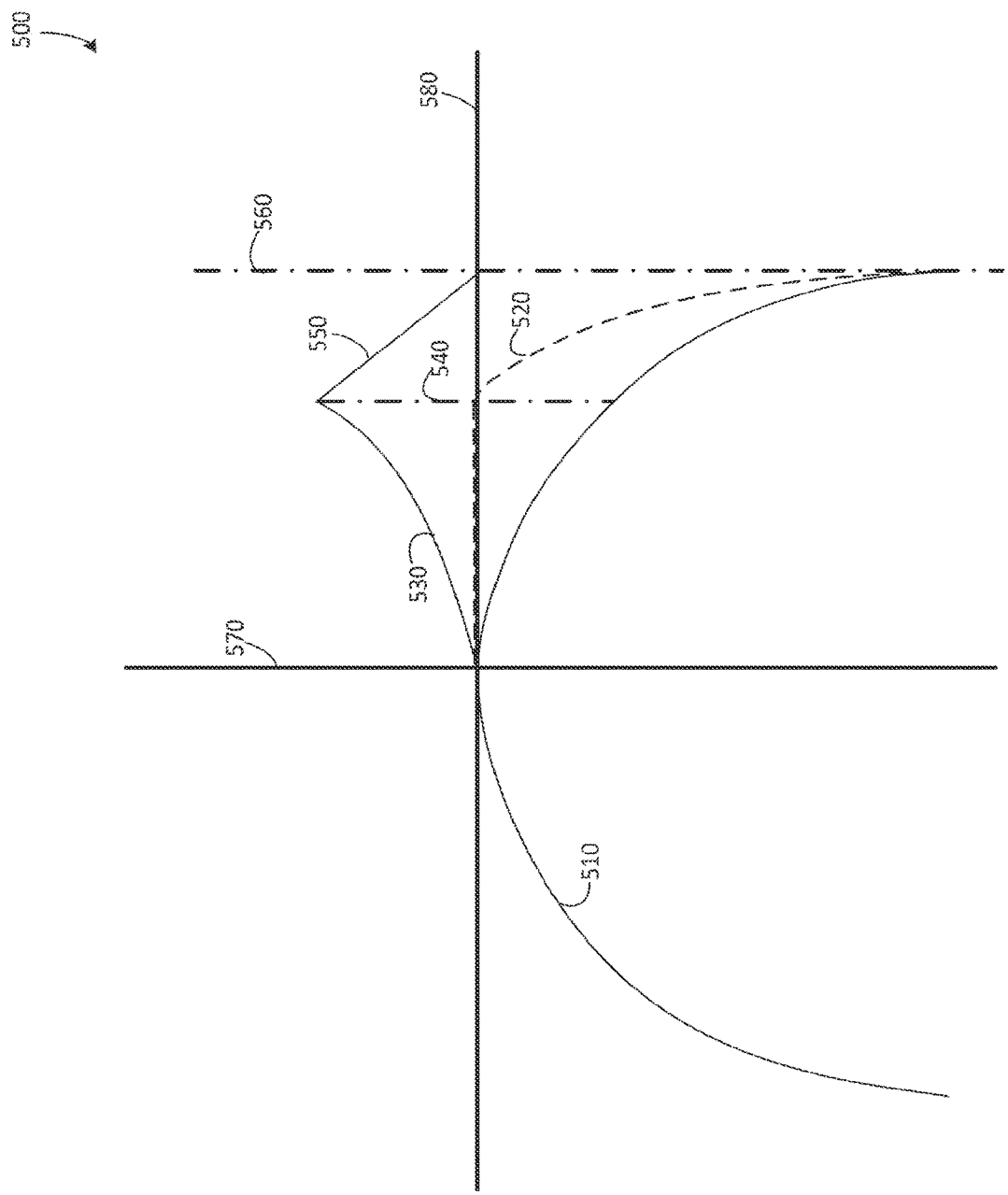
FIG. 5 shows an example of distortion correction.

FIG. 5 shows an example of a distortion correction curve 500 for generating the modified image (e.g., representation 400 of the modified image in FIG. 4). In some implementations, the distortion for a high field of view image is radially symmetric. For example, the distortion shown in representations 300 and 400 of FIGS. 3-4 is increases radially from the center toward the periphery of the source image. The graph 500 of FIG. 5 represents an example of a distortion correction curve for such a distortion. Axis 570 represents a magnitude of the distortion/correction, and axis 580 represents a distance from the center of the image.

In the example of FIG. 5, the distortion is represented by the function 510. In some implementations, the distortion is a quadratic function of the distance from the center of the image. However, the distortion in other cases may be represented using other functions. The distortion can be regular, as shown in FIG. 5. In some implementations, the distortion is irregular, for example, one that cannot be represented using a simple function.

The line 560 represents an edge of the image (e.g., both the modified image and the source image). The function shown by the curve 530 represents an inversion of the distortion 510 inside the central region (e.g., central region 420 of FIG. 4). The inversion of the distortion cancels out the distortion and results in a substantially distortion-corrected representation of the surgical scene in the central region. The line 540 represents a distance of the boundary of the central region from the center of the image. This particular example assumes a circular central region where the same distortion correction is applied along the x and y axes of the image. In the peripheral region (e.g., the peripheral region 430 of FIG. 4) between the line 540 and the edge 560 of the image, a linear correction is applied, the correction linearly decreasing from a peak correction value at boundary of the central region to zero at the edge 560 of the modified image. In some cases, this can ensure a smooth transition between the corrected and un-corrected regions of the image, making the transition appear less abrupt to a viewer. In some implementations, the distortion correction can be substantially equal to zero throughout the peripheral region.

The effect of the correction in the modified image is represented by line 520, which represents a sum of the distortion and the correction at various distances from the center of the image. Inside the central region 420, the line 520 shows no distortion in the modified image. In the peripheral region 430 (e.g., between the boundary of the central region and the edge 560 of the modified image), the modified image exhibits distortion that increases with increasing distance from the center of the image. The linear correction 550 in the peripheral region smooths the transition from the central region 420 to the peripheral region 430 so that the surgical scene in the central region 420 and the peripheral region 430 appear to blend. The smooth transition from the central region 420 to the peripheral region 430 enables a situational awareness of the surgical scene in the peripheral region without causing a potentially disorienting effect of having a sharp border between the central region 420 and the peripheral region 430. In some implementations, the corrections 530 inside the central region 420 and the correction 550 applied in the peripheral region 430 can be a smooth function, rather than a function including a discontinuity.

In some implementations, correction 550 can include further distorting the peripheral region 430. For example, when the central region 420 field of view is greater than a threshold, the peripheral region 430 is further distorted (e.g., compressed) to preserve the information included in the peripheral region 430. In some implementations, the peripheral region 430 is further distorted as a function of the size of the central region 420.

Figure 6:
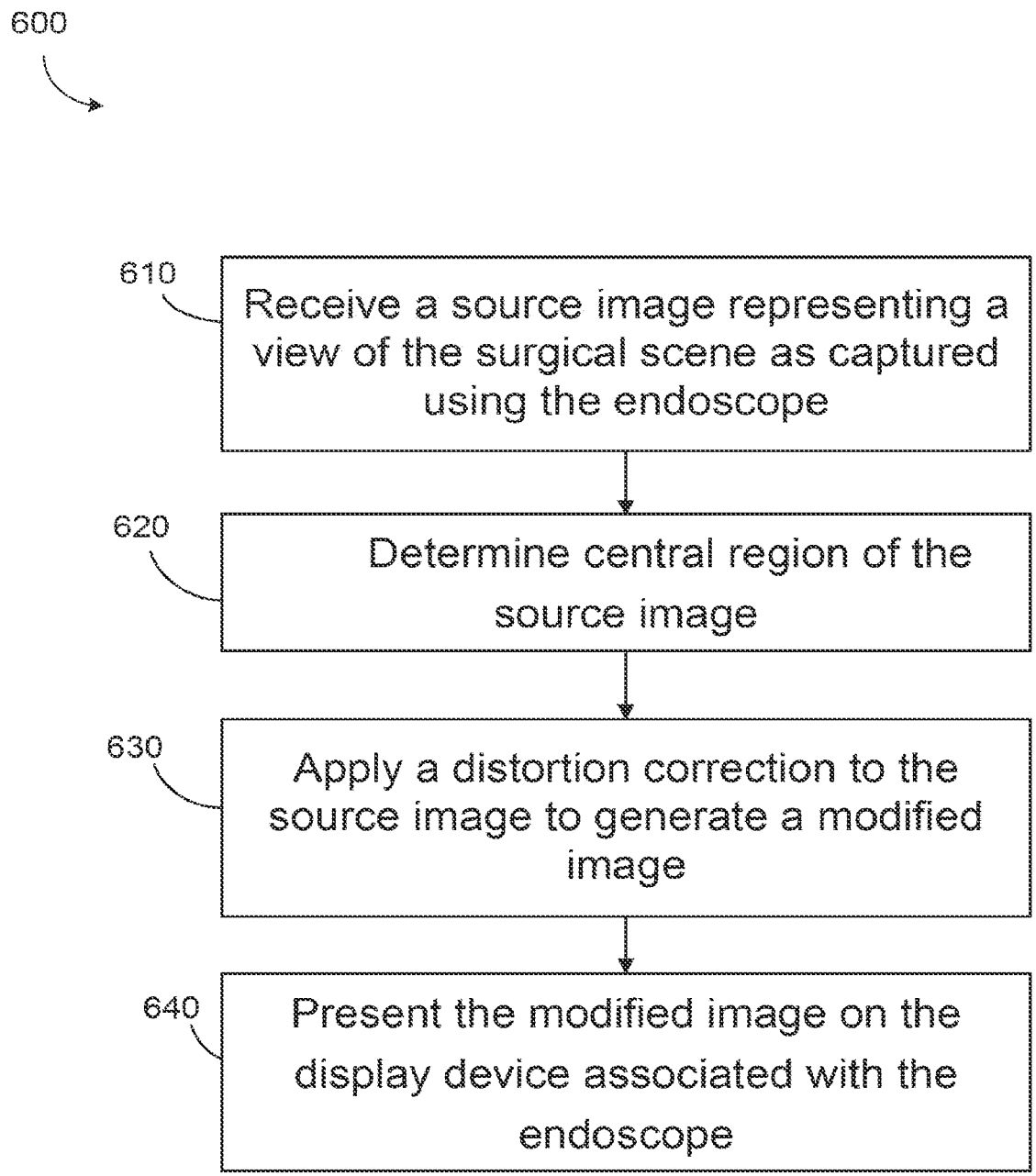
FIG. 6 is a flowchart illustrating an example process of correcting distortion in a source image to generate a modified image.

FIG. 6 is a flowchart illustrating an example process 600 that employs distortion correction of endoscopic images in computer-assisted tele-operated surgery. In some implementations, at least a portion of the process 600 may be executed by a processing device associated with a surgeon's console of a robotic surgical system. Operations of the process 600 can include receiving (610) a source image representing a view of the surgical scene as captured using the endoscope. The source image includes a distortion effect. Receiving the image can include, for example, receiving a source image depicting a surgical scene during a telesurgery operation. One or more characteristics of the distortion effect can be known in advance of the telesurgery operation. For example, the distortion effect can be caused by a lens of the endoscope in order to increase a field of view of the surgical scene that is captured into the source image. In some implementations, the distortion is radial-based and increases from the center of the source image to the edges of the source image.

The operations of process 600 further include determining (620) a central region of the source image. Determining the central region includes determining the size, shape, and position of the central region. The central region includes a region of interest or focus of surgical scene. In some implementations, the size, shape, and/or position of the central region are determined automatically. In some implementations, the size, shape, and/or position of the central region are preprogrammed before the telesurgery. In some implementations, the position of the central region is based on signals received from one or more sensors of the telesurgery system. For example, the position of the central region can be based on signals received from a gaze-tracking system. The central region is positioned where a user is looking on a display device. In another example, the position of the central region is fixed in the center of the display and/or the image. In another example, the source image is processed to detect a feature of the source image, and the central region is positioned to overlap the detected feature in the source image. The feature can be a surgical instrument, target of the telesurgery operation, and so forth. In yet another example, the size of the central region is adjusted based on a distance of a user from the display device (e.g., display device 45 of FIG. 2A). In some implementations, the shape of the central region is approximately elliptical. In some implementations, the size and/or shape of the central region is adjusted over time.

The rest of the source image that is not the central region includes the peripheral region. In some implementations, the peripheral region surrounds the central region. In some implementations, the central region is positioned at an edge of the image. In some implementations, the central region is positioned at a corner of the image.

Operations of the process 600 further include applying (630) a distortion correction to source image to generate a modified image. A first degree of distortion correction is applied to the central region. A second degree of distortion correction is applied to the peripheral region. The first degree of distortion correction is greater than the second degree of correction. In some implementations, the distortion correction includes a correction function in which the degree of correction is a function of location in the source image with respect to a reference point in the source image. For example, the degree of correction changes non-linearly in the central region and linearly in the peripheral region. In some implementations, the degree of distortion correction changes based on a quadratic function. When the central region is exactly in the center of the source image, the degree of correction is increased from the center of the central region toward a boundary of the central region. The first degree of correction need not be uniform over the entire central region, but can be based on the distortion being corrected. The second degree of distortion correction is different from the first degree of distortion correction. In some implementations, the second degree of distortion correction is based on a linear function. In some implementations, the function is not exactly linear, but can include a smoothing portion near the boundary of the central region to smooth the transition from the first degree of correction to the second degree of correction. The smoothing correction can reduce a potential disorientation effect caused by viewing a sharp discontinuity in the distortion correction between the central region and the peripheral region. The smoothing correction can resolve a discontinuity between the first degree of distortion correction in the central region and the second degree of distortion correction in the peripheral region.

The modified image is generated to include both the central region and the peripheral region surrounding the central region. The modified image thus includes a portion (the central region) that represents the surgical scene substantially distortion-free (e.g., in high fidelity and resolution), while maintaining a peripheral region that provides a lower-resolution representation of the surgical scene surrounding the central region and providing a situational awareness for the central region. In some implementations, other modifications can be made to the modified image. For example, a zoom transform can be applied to the central region.

Operations of the process 600 further include presenting (640) the modified image on the display device associated with the endoscope. The process 600 can be repeated for each frame of a video captured by the endoscope.

The functionality described herein, or portions thereof, and its various modifications (hereinafter "the functions") can be implemented, at least in part, via a computer program product, e.g., a computer program tangibly embodied in an information carrier, such as one or more non-transitory machine-readable media or storage device, for execution by, or to control the operation of, one or more data processing apparatus, e.g., a programmable processor, a DSP, a microcontroller, a computer, multiple computers, and/or programmable logic components.

A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one or more processing devices at one site or distributed across multiple sites and interconnected by a network.

Actions associated with implementing all or part of the functions can be performed by one or more programmable processors or processing devices executing one or more computer programs to perform the functions of the processes described herein. All or part of the functions can be implemented as, special purpose logic circuitry, e.g., an FPGA and/or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. Components of a computer include a processor for executing instructions and one or more memory devices for storing instructions and data.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Elements described in detail with reference to one embodiment, implementation, or application optionally may be included, whenever practical, in other embodiments, implementations, or applications in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A surgical system, comprising:
    a display device;
    an endoscope; and
    one or more processing devices configured to operate the surgical system to perform a process comprising:
        receiving, from the endoscope, a source image representing a view of a surgical scene as captured using the endoscope;
        receiving a gaze location of a user of the surgical system;
        determining a first region of the source image based on the gaze location, wherein a second region of the source image at least partially surrounds the first region and includes a source distortion;
        applying a distortion correction to at least a portion of the source image to generate a modified image by applying a first degree of distortion correction in the first region and a second degree of distortion correction in the second region, wherein the second degree of distortion correction preserves the source distortion in at least a portion of the second region; and
        displaying the modified image on the display device associated with the endoscope.

2. The surgical system of claim 1, wherein the first region of the modified image is displayed at a side portion of the display device.

3. The surgical system of claim 2, wherein the modified image is centered about a center of the display device and wherein the first region of the modified image overlaps a center of the display device.

4. The surgical system of claim 1, wherein the modified image is centered about a center of the display device and wherein the first region of the modified image is displayed on a portion of the display device that does not include the center of the display device.

5. The surgical system of claim 1, wherein a display location of the first and second regions on the display device is dynamically adjustable based on a change of the gaze location.

6. The surgical system of claim 1, wherein the process further comprises:
   detecting a distance of the user from the display device, wherein a size of the first region is determined based on the detected distance.

7. The surgical system of claim 1, wherein the process further comprises:
   recognizing a feature present in the source image, wherein a size of the first region is determined based on the recognized feature.

8. The surgical system of claim 1, wherein the distortion correction comprises a correction function in which a degree of correction is a function of location with respect to a reference point in the source image.

9. The surgical system of claim 8, wherein the degree of correction varies non-linearly in the first region, and linearly in the second region.

10. The surgical system of claim 1, wherein the process further comprises:
    applying a smoothing correction to the modified image near a border of the first region, the smoothing correction resolving a discontinuity between the first degree of distortion correction in the first region and the second degree of distortion correction in the second region.

11. A method of presenting an image of a portion of a surgical scene on a display device associated with an endoscope, the method comprising:
    receiving, from the endoscope, a source image representing a view of a surgical scene as captured using the endoscope;
    receiving a gaze location of a user;
    determining a first region of the source image based on the gaze location, wherein a second region of the source image at least partially surrounds the first region and includes a source distortion;
    applying a distortion correction to at least a portion of the source image to generate a modified image by applying a first degree of distortion correction in the first region and a second degree of distortion correction to the second region, wherein the second degree of distortion correction preserves the source distortion in at least a portion of the second region; and
    displaying the modified image on the display device associated with the endoscope.

12. The method of claim 11, wherein the first region of the modified image is displayed at a side portion of the display device.

13. The method of claim 12, wherein the modified image is centered about a center of the display device and wherein the first region of the modified image overlaps the center of the display device.

14. The method of claim 11, wherein the modified image is centered about a center of the display device and wherein the first region of the modified image is displayed on a portion of the display device that does not include the center of the display device.

15. The method of claim 11, wherein a display location of the first and second regions on the display device is dynamically adjustable based on a change of the gaze location.

16. The method of claim 11, further comprising:
    detecting a distance of the user from the display device, wherein a size of the first region is determined based on the detected distance.

17. The method of claim 11, further comprising:
    recognizing a feature present in the source image, wherein a size of the first region is determined based on the recognized feature.

18. The method of claim 11, wherein the distortion correction comprises a correction function in which a degree of correction is a function of location with respect to a reference point in the source image.

19. The method of claim 18, wherein the degree of correction varies non-linearly in the first region, and linearly in the second region.

20. The method of claim 11, further comprising:
    applying a smoothing correction to the modified image near a border of the first region, the smoothing correction resolving a discontinuity between the first degree of distortion correction in the first region and the second degree of distortion correction in the second region.

* * * * *

UNITED STATES PATENT AND TRADEMARK OFFICE
CERTIFICATE OF CORRECTION

PATENT NO. : 12,324,561 B2
APPLICATION NO. : 18/600331
DATED : June 10, 2025
INVENTOR(S) : Jason Paul Watson It is certified that error appears in the above-identified patent and that said Letters Patent is hereby corrected as shown below:

In the Specification

Column 1, Line 10, change "17/270,315" to -- 17/270,316 --

Signed and Sealed this
Second Day of September, 2025

Coke Morgan Stewart
*Acting Director of the United States Patent and Trademark Office*